(12) United States Patent
Ishii et al.

(10) Patent No.: US 8,450,520 B2
(45) Date of Patent: May 28, 2013

(54) PROCESS FOR PREPARATION OF 2-FLUOROACRYLIC ESTERS

(75) Inventors: Akihiro Ishii, Kawagoe (JP); Takako Yamazaki, Kawagoe (JP); Hideyuki Tsuruta, Kawagoe (JP); Satoru Miyazawa, Kawagoe (JP); Michitaka Ootani, Kawagoe (JP); Takashi Ootsuka, Kawagoe (JP); Mikihiro Takahashi, Ube (JP); Masataka Fujimoto, Ube (JP)

(73) Assignee: Central Glass Company, Limited, Ube-shi (JP)

( * ) Notice: Subject to any disclaimer, the term of this patent is extended or adjusted under 35 U.S.C. 154(b) by 6 days.

(21) Appl. No.: 13/266,008

(22) PCT Filed: Mar. 23, 2010

(86) PCT No.: PCT/JP2010/054914
§ 371 (c)(1),
(2), (4) Date: Oct. 24, 2011

(87) PCT Pub. No.: WO2010/134382
PCT Pub. Date: Nov. 25, 2010

(65) Prior Publication Data
US 2012/0059187 A1 Mar. 8, 2012

(30) Foreign Application Priority Data
May 19, 2009 (JP) .................................. 2009-120478
Feb. 26, 2010 (JP) .................................. 2010-041158

(51) Int. Cl.
*C07C 67/287* (2006.01)
(52) U.S. Cl.
USPC .......................................... 560/227; 560/229
(58) Field of Classification Search
CPC combination set(s) only.
See application file for complete search history.

(56) References Cited

U.S. PATENT DOCUMENTS
2010/0087673 A1  4/2010  Ishii et al.

FOREIGN PATENT DOCUMENTS

| JP | 2001-139513 A | 5/2001 |
| JP | 2001-139519 A | 5/2001 |
| JP | 2001-172223 A | 6/2001 |
| JP | 2008-201770 A | 9/2008 |

OTHER PUBLICATIONS

Takeuchi et al, Chemical and Pharmaceutical Bulletin of Japan, Chemistry of Novel Compounds of Multifunctional Carbon Structure. VI. Synthetic Studies and 19F-Nuclear Magnetic Resonance Investigation of Novel alpha,alpha-Disubstituted Fluoroacetates, 1990, 38(9), pp. 2404-2408.*
Corresponding International Search Report with English Translation dated May 18, 2010 (five (5) pages).
Form PCT/ISA/237 (three (3) pages).
Elke Fritz-Langhals et al., "Simple Synthesis of Optically Active 2-Fluoropropanoic Acid and Analogs of High Enantiomeric Purity", Tetrahedron Letters, 1993, pp. 293-296, vol. 34, Great Britain.
George A. Olah et al., "Synthetic Methods and Reactions. 63.[1] Pyridinium Poly(hydrogen fluoride) (30% pyridine-70% Hydrogen Fluoride): A Convenient Reagent for Organic Fluorination Reactions", J. Org. Chem., 1979, pp. 3872-3881, vol. 44, No. 22, American Chemical Society.
Jikken Kagaku Koza, "Synthesis of Organic Compounds [1]:—Hydrocarbons and Halides", The Chemical Society of Japan, (2004), pp. 374-443, Maruzen Co., Ltd.
Yoshio Takeuchi et al., "Chemistry of Novel Compounds with Multifunctional Carbon Strucure. VI. [1]) Synthetic Studies and [19]F-Nuclear Magnetic Resonance Investigation of Novel α,α-Disubstituted Fluoroacetates", Chem. Pharm. Bull. (1990), pp. 2404-2408, vol. 38, No. 9, Pharmaceutical Society of Japan.
Extended European Search Report dated Sep. 27, 2012 (six (6) sheets).
Takeuchi et al., "Synthetic studies for novel structure of α-nitrogenously functionalized α-fluorocarboxylic acids. Part 1. The first synthesis and reactions of N-protected α-fluoroglycines", Journal of the Chemistry Society, Perkin Transactions: Organic and Bio-Organic Chemistry, 1991, pp. 49-53, XP2683718 (five (5) sheets).

* cited by examiner

*Primary Examiner* — Paul A Zucker
(74) *Attorney, Agent, or Firm* — Crowell & Moring LLP

(57) ABSTRACT

According to the present invention, there is provided a production process of a 2-fluoroacrylic ester including: a bromination step of converting a 2-fluoropropionic ester to a 2-bromo-2-fluoropropionic ester by reaction of the 2-fluoropropionic ester with a nitrogen-bromine bond-containing brominating agent in the presence of a radical initiator; and a dehydrobromination step of reacting the 2-bromo-2-fluoropropionic ester with a base. It is not necessary in this process to adopt very-low-temperature conditions and to use a stoichiometric amount of expensive reagent. The target 2-fluoroacrylic ester can be thus produced at low cost.

11 Claims, No Drawings

PROCESS FOR PREPARATION OF 2-FLUOROACRYLIC ESTERS

TECHNICAL FIELD

The present invention relates to a process for production of 2-fluoroacrylic esters, which are important as intermediates for pharmaceutical and agricultural chemicals and as monomers for functional polymers.

BACKGROUND ART

It is known that 2-fluoroacrylic esters are important as intermediates for pharmaceutical and agricultural chemicals and as monomers for functional polymers. Patent Publication 1 discloses, as a conventional production technique relevant to the present invention, a process of producing 2-bromo-2-fluoropropionic ester by reaction of 2-fluoropropionic ester with carbon tetrabromide or bromine in the presence of a base. Further, Patent Document 2 discloses a process for producing 2-fluoroacrylic ester by dehydrobromination reaction of 2-bromo-2-fluoropropionic ester in the presence of a basic compound.
Prior Art Documents
Patent Documents
Patent Document 1: Japanese Laid-Open Patent Publication No. 2001-139519
Patent Document 2: Japanese Laid-Open Patent Publication No. 2001-172223
Problems to be Solved by the Invention In the production process of Patent Document 1, it is necessary to conduct the reaction under very-low-temperature conditions (i.e. at a temperature not exceeding −70° C.) as there occurs an unstable anion by the reaction of the 2-fluoropropionate with the base. It is also necessary to use a stoichiometric amount of expensive organic lithium compound (such as lithium dialkylamide or n-butyl lithium) as the base.

In the production process of Patent Document 2, it is necessary to use a nitrogen-containing basic compound against the ester and, particularly in the case of expecting high yield, use a stoichiometric amount of expensive 1,8-diazabicyclo[5.4.0]undec-7-ene (DBU).

Accordingly, there has been a strong demand for an industrial production process of 2-fluoroacrylic esters that does not need very-low-temperature equipment and expensive reagent.

It is therefore an object of the present invention to solve the above prior art problems and provide an industrial production process of 2-fluoroacrylic esters that does not need very-low-temperature equipment and expensive reagent.
Means for Solving the Problems The present inventors have made extensive researches in view of the above prior art problems and, as a result, have found that it is possible to produce a 2-fluoroacrylic ester by reacting a 2-fluoropropionic ester with a nitrogen-bromine bond-containing brominating agent in the presence of a radical initiator (bromination reaction), and then, reacting the 2-bromo-2-fluoropropionic ester with a base (dehydrobromination reaction).

It is preferable that, in the ester moiety of the 2-fluoropropionic ester, R is either a methyl group, an ethyl group, a 2,2,2-trifluoroethyl group or a 1,1,1,3,3,3-hexafluoroisopropyl group. The 2-fluoropropionic ester in which R is methyl, ethyl, 2,2,2-trifluoroethyl or 1,1,1,3,3,3-hexafluoroisopropyl can be easily obtained on a large scale. Further, the 2-fluoroacrylic ester produced from such a 2-fluoropropionic ester is particularly important and preferred in terms of usability.

As the nitrogen-bromine bond-containing brominating agent, N-bromosuccinimide (NBS) is preferred. This brominating agent can be easily obtained on a large scale and at low cost and exhibits good reactivity. As the radical initiator for the bromination reaction, 2,2'-azobisisobutyronitrile (AIBN), 1,1'-azobis(cyclohexane-1-carbonitrile) (V-40) and benzoyl peroxide (BPO) are preferred. These radical initiators can be easily obtained on a large scale and at low cost and each exhibit good reactivity.

It is further preferable to use, as the base in the dehydrobromination reaction, a stoichiometric amount of alkali metal carbonate or tri-n-butylamine in the presence of a catalytic amount of 1,8-diazabicyclo[5.4.0]undec-7-ene (DBU). This base allows the reaction to proceed at low cost even on a large scale while maintaining good reactivity.

In order to prevent self-polymerization of the 2-fluoroacrylic ester, the dehydrobromination reaction and the distillation purification may be performed in the presence of a polymerization inhibitor. As the polymerization inhibitor, phenothiazine, hydroquinone and 2,6-di-tert-butyl-4-methylphenol (BHT) are preferred. These polymerization inhibitors can be easily obtained on a large scale and at low cost and each show good self-polymerization prevention effects. Furthermore, the distillation purification may be performed by entraining air or oxygen in the 2-fluoroacrylic ester (this distillation operation is hereinafter called "aeration distillation") in order to prevent self-polymerization of the 2-fluoroacrylic ester. It is preferable in the aeration distillation to entrain air in the 2-fluoroacrylic ester so that the distillation can be performed safely with less equipment load for equivalent self-polymerization prevention effects.

As mentioned above, there have been found the useful techniques for production of the 2-fluoroacrylic ester. The present invention is based on these findings.

Namely, the present invention includes the following features.

[Inventive Feature 1]

A process of producing a 2-fluoroacrylic ester of the general formula [3], comprising:

a bromination step of converting a 2-fluoropropionic ester of the general formula [1] to a 2-bromo-2-fluoropropionic ester of the general formula [2] by reaction of the 2-fluoropropionic ester with a nitrogen-bromine bond-containing brominating agent in the presence of a radical initiator; and a dehydrobromination step of reacting the 2-bromo-2-fluoropropionic ester with a base

[Chem. 1]

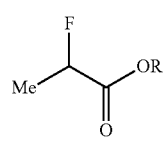

[1]

[Chem. 2]

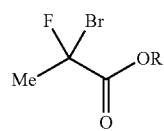

[2]

-continued

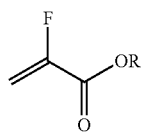

[3]

where Me represents a methyl group; and R represents an alkyl group or a fluorine-substituted alkyl group.

[Inventive Feature 2]

The process of producing the 2-fluoroacrylic ester according to Inventive Feature 1, wherein, in an ester moiety of the ester, R is either a methyl group, an ethyl group, a 2,2,2-trifluoroethyl group or a 1,1,1,3,3,3-hexafluoroisopropyl group.

[Inventive Feature 3]

The process of producing the 2-fluoroacrylic ester according to Inventive Feature 1 or 2, wherein the nitrogen-bromine bond-containing brominating agent used in the bromination step is N-bromosuccinimide (NBS).

[Inventive Feature 4]

The process of producing the 2-fluoroacrylic ester according to any one of Inventive Features 1 to 3, wherein the radical initiator used in the bromination step is either 2,2'-azobisisobutyronitrile (AIBN), 1,1'-azobis(cyclohexane-1-carbonitrile) (V-40) or benzoyl peroxide (BPO).

[Inventive Feature 5]

The process of producing the 2-fluoroacrylic ester according to any one of Inventive Features 1 to 4, wherein an alkali metal carbonate is used stoichiometrically in the presence of a catalytic amount of 1,8-diazabicyclo[5.4.0]undec-7-ene (DBU) as the base in the dehydrobromination step.

[Inventive Feature 6]

The process of producing the 2-fluoroacrylic ester according to any one of Inventive Features 1 to 4, wherein tri-n-butylamine is used stoichiometrically in the presence of a catalytic amount of 1,8-diazabicyclo[5.4.0]undec-7-ene (DBU) as the base in the dehydrobromination step.

[Inventive Feature 7]

The process of producing the 2-fluoroacrylic ester according to any one of Inventive Features 1 to 6, wherein the dehydrobromination step is performed in the presence of a polymerization inhibitor.

[Inventive Feature 8]

The process of producing the 2-fluoroacrylic ester according to Inventive Feature 7, wherein the polymerization inhibitor is either phenothiazine, hydroquinone or 2,6-di-tert-butyl-4-methylphenol (BHT).

[Inventive Feature 9]

The process of producing the 2-fluoroacrylic ester according to any one of Inventive Features 1 to 8, further comprising subjecting the 2-fluoroacrylic ester to distillation purification in the presence of a polymerization inhibitor.

[Inventive Feature 10]

The process of producing the 2-fluoroacrylic ester according to Inventive Feature 9, wherein the polymerization inhibitor is either phenothiazine, hydroquinone or 2,6-di-tert-butyl-4-methylphenol (BHT).

[Inventive Feature 11]

The process of producing the 2-fluoroacrylic ester according to any one of Inventive Features 1 to 10, further comprising subjecting the 2-fluoroacrylic ester to distillation purification while entraining air or oxygen in the 2-fluoroacrylic ester.

In the production process of the present invention, there are no need to adopt very-low-temperature conditions and no need to use a stoichiometric amount of expensive reagent. It is therefore possible that the target 2-fluoroacrylic ester can be produced at low cost. As moderate production conditions are adopted in the present invention, almost no hydrolysis of the ester moiety occurs throughout the bromination and dehydrobromination steps. This eliminates the need for complicated operation of converting the corresponding carboxylic acid to the target ester compound. Further, the production process of the present invention is suitable in terms of toxic waste reduction as the 2-fluoropropionic ester can be used in an excessive amount so as to serve not only as the raw substrate material but also as a reaction solvent in the bromination step and thereby avoid the use of a chlorinated reaction solvent such as carbon tetrachloride frequently used for halogenation.

BEST MODES FOR CARRYING OUT THE INVENTION

Hereinafter, the present invention will be described in detail below.

The production process of the present invention includes: a bromination step of converting a 2-fluoropropionic ester of the general formula [1] to a 2-bromo-2-fluoropropionic ester of the general formula [2] by reaction of the 2-fluoropropionic ester with a nitrogen-bromine bond-containing brominating agent in the presence of a radical initiator; and a dehydrobromination step of converting the 2-bromo-2-fluoropropionic ester to a 2-fluoroacrylic ester of the general formula [3] by reaction of the 2-bromo-2-fluoropropionic ester with a base.

[Chem. 4]

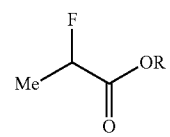

[1]

[Chem. 5]

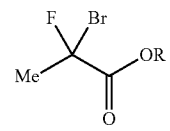

[2]

[Chem. 6]

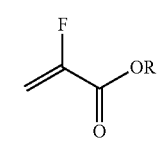

[3]

First, the bromination step will be explained in detail below.

In the 2-fluoropropionic ester of the general formula [1], Me represents a methyl group; and R represents an alkyl group or a fluorine-substituted alkyl group. Examples of the alkyl group are those having a carbon number of 1 to 18. The alkyl group can be straight-chained, branched or cyclic (in the case where the carbon number is 3 or more). Examples of the fluorine-substituted alkyl group are those obtained by substitution of any number of fluorine atoms onto any of carbon atoms of the alkyl group. Among others, a methyl group, an ethyl group, a 2,2,2-trifluoroethyl group or a 1,1,1,3,3,3-hexafluoroisopropyl group are preferred. Particularly preferred are methyl and ethyl. Although the 2-position carbon atom of the 2-fluoropropionic ester of the general formula [1] is an asymmetric carbon atom, this carbon is finally converted to a $sp^2$ carbon. The 2-fluoropropionic ester of the general formula [1] is not thus limited to either an optically active substance (R form or S form) or a racemic mixture. Both of the optically active substance and the racemic mixture can be used equally. It is preferable to use the racemic mixture as the racemic mixture can be easily obtained on a large scale and at low cost. As a matter of course, the optically active substance may alternatively be used.

The 2-fluoropropionic ester of the general formula [1] can be prepared in the same manners as described in Japanese Laid-Open Patent Publication No. 2008-201770; Tetrahedron Letters (U.K.), 1993, Vol. 34, P. 293-296; J. Org. Chem. (U.S.), 1979, Vol. 44, P. 3872-3881 etc.

Examples of the nitrogen-bromine bond-containing brominating agent are N-bromoacetamide, N-bromosuccinimide (NBS), N-bromophthalimide and 1,3-dibromo-5,5-dimethylhydantoin. Among others, N-bromosuccinimide (NBS) is preferred. In the present specification, there are listed typical examples of the nitrogen-bromine bond-containing brominating agent. As the nitrogen-bromine bond-containing brominating agent, there can suitably be used any of those described in Jikken Kagaku Koza 13, Fifth Edition, Synthesis of Organic Compounds [I], Hydrocarbons and Halides, P. 374-443, 2004, edited by The Chemical Society of Japan and published by Maruzen Co., Ltd.

It suffices to use the nitrogen-bromine bond-containing brominating agent in an amount of 0.05 mol or more per 1 mol of the 2-fluoropropionic ester of the general formula [1]. The amount of the nitrogen-bromine bond-containing brominating agent used is preferably 0.1 to 10 mol, more preferably 0.15 to 5 mol, per 1 mol of the 2-fluoropropionic ester of the general formula [1]. In some cases, the nitrogen-bromine bond-containing brominating agent may preferably be charged into a reaction system over a plurality of times. It is alternatively feasible to charge the nitrogen-bromine bond-containing brominating agent into the reaction system at one time.

Examples of the radical initiator are: azo radical initiators such as 2,2'-azobisisobutyronitrile (AIBN), 2,2'-azobis(2-methylbutyronitrile), 2,2'-azobis(2,4-dimethylvaleronitrile) (V-65), 1,1'-azobis(cyclohexane-1-carbonitrile) (V-40), dimethyl 2,2'-azobis(2-methylpropionate), 4,4'-azobis(4-cyanovaleric acid) and 2,2'-azobis(2-amidinopropane)dihydrochloride; and peroxide radical initiators such as benzoyl peroxide (BPO), tert-butyl peroxypivalate, di-tert-butyl peroxide, i-butyryl peroxide, lauroyl peroxide, succinic acid peroxide, dicinnamyl peroxide, di-n-propyl peroxydicarbonate, tert-butyl peroxyallylmonocarbonate, hydrogen peroxide and ammonium persulfate. Among others, 2,2'-azobisisobutyronitrile (AIBN), 1,1'-azobis(cyclohexane-1-carbonitrile) (V-40) and benzoyl peroxide (BPO) are preferred. Particularly preferred is 1,1'-azobis(cyclohexane-1-carbonitrile) (V-40). It is necessary to select the radical initiator in consideration of ease of separation of the target compound by purification from any decomposition product derived from the radical initiator. From this point of view, 1,1'-azobis(cyclohexane-1-carbonitrile) (V-40) is most preferred among the preferred radical initiators such as 2,2'-azobisisobutyronitrile (AIBN), 1,1'-azobis(cyclohexane-1-carbonitrile) (V-40) and benzoyl peroxide (BPO). These radical initiators are commercially available and can be easily obtained on a large scale and at low cost.

It suffices to use the radical initiator in an amount of 0.0001 mol or more per 1 mol of the 2-fluoropropionic ester of the general formula [1]. The amount of the radical initiator used is preferably 0.001 to 0.5 mol, more preferably 0.005 to 0.4 mol, per 1 mol of the 2-fluoropropionic ester of the general formula [1]. As the radical initiator has a specific half life, it is feasible to charge the radical initiator into the reaction system over a plurality of times according to the half life of the radical initiator. As a matter of course, it is alternatively feasible to charge the radical initiator into the reaction system at one time.

There can be used a reaction solvent. Examples of the reaction solvent are halogenated solvents such as methylene chloride, chloroform, carbon tetrachloride, 1,2-dichloroethane, tetrachloroethane (1,1,2,2- or 1,1,1,2-tetrachloroethane), $\alpha,\alpha,\alpha$,-trifluorotoluene (BTF) and dichlorobenzotrifluoride (2,4-, 2,5- or 3,4-dichlorobenzotrifluoride). Among others, carbon tetrachloride, $\alpha,\alpha,\alpha$,-trifluorotoluene (BTF) and 2,4-dichlorobenzotrifluoride are preferred. Particularly preferred is $\alpha,\alpha,\alpha$,-trifluorotoluene (BTF). These reaction solvents can be used solely or in combination thereof.

It suffices to use the reaction solvent in an amount of 7 L or less per 1 mol of the 2-fluoropropionic ester of the general formula [1]. The amount of the reaction solvent used is preferably 5 L or less, more preferably 3 L or less, per 1 mol of the 2-fluoropropionic ester of the general formula [1]. The lower limit of the amount of the reaction solvent is not specifically defined as the present reaction step can be performed without using the reaction solvent.

In the bromination step, it is feasible to use the 2-fluoropropionic ester of the general formula [1] in an excessive amount and thereby avoid the use of the halogenated reaction solvent. The excessive 2-fluoropropionic ester can be recovered with high yield by fractional distillation and then reused. It has been newly found that, in the suitable combination of methyl 2-fluoropropionate and N-bromosuccinimide (NBS), it is possible by using the methyl 2-fluoropropionate excessively without using the reaction solvent to significantly improve the solubility of N-bromosuccinimide (NBS) and succinimide by-produced therewith during the reaction and remarkably reduce the load of stirring equipment that becomes a problem in solid-liquid reaction. In the case of using the reaction solvent (e.g. carbon tetrachloride), most of the succinimide gets deposited and becomes a cause of equipment load for favorable stirring operation. Further, the total amount of the reaction liquid may be reduced to obtain higher productivity in the case of using of the 2-fluoropropionic ester excessively without using the reaction solvent. It is thus one preferred embodiment of the present invention to use the 2-fluoropropionic ester excessively without using the reaction solvent.

In the case of using the 2-fluoropropionic ester of the general formula [1] excessively without using the reaction solvent, it suffices that amount of excessive use of the 2-fluoropropionic ester is 0.1 mol or more per 1 mol of the 2-fluoropropionic ester used as the raw substrate material. The amount of excessive amount of the 2-fluoropropionic ester is preferably 0.2 to 5 mol, more preferably 0.3 to 4 mol, per 1 mol of the 2-fluoropropionic ester used as the raw substrate material. (It means that, when the amount of excessive use of the 2-fluoropropionic ester is 1 mol, the total amount of use of the 2-fluoropropionic ester including the amount of the 2-fluoropropionic ester used as raw substrate material is substantially 2 mol.)

It suffices that the reaction temperature is in the range of 0 to 130° C. The reaction temperature is preferably in the range of 10 to 120° C., more preferably 20 to 110° C.

It suffices that the reaction time is in the range of 120 hours or less. As the reaction time varies depending on the raw substrate material, the reagent, the reaction aid and the reaction conditions, it is desirable to determine the time at which there can be seen almost no consumption of the raw substrate material as the end of the reaction while monitoring the progress of the reaction by any analytical means such as gas chromatography, liquid chromatography or nuclear magnetic resonance.

In the bromination step, the rate of the reaction may be improved by performing the reaction in the presence of a catalytic amount of bromine ($Br_2$). In the case where the reaction system significantly shifts to the acidic side, it is feasible to perform the reaction while controlling the pH of the reaction system by the addition of an inorganic base such as sodium hydrogencarbonate, potassium hydrogencarbonate, sodium carbonate, potassium carbonate or magnesium oxide. In the case where the concentration of fluorine ions in the reaction system significantly rises, it is feasible to perform the reaction while controlling the fluorine-ion concentration of the reaction system by the addition of a defluorinating agent such as calcium carbonate, calcium hydroxide, calcium chloride or silica gel. The use of these additives is not essential in the present reaction step. However, the desired effects (such as good reaction rate, weak acid to neutral reaction range, low fluorine-ion concentration etc.) can be obtained by the adoption of the suitable reaction conditions.

The target 2-bromo-2-fluoropropionic ester of the general formula [2] can be obtained from the reaction terminated liquid by any ordinary post treatment operation for organic synthesis.

Preferably, it is feasible to recover a crude product of the 2-bromo-2-fluoropropionic ester easily with high yield by filtering out any solid matter from the reaction terminated liquid (after depositing the solid matter by cooling as needed), and then, directly subjecting the resulting filtrate to distillation under reduced pressure. In the case of using N-bromosuccinimide (NBS) as the nitrogen-bromine bond-containing brominating agent, most of the recovered solid matter is succinimide. The succinimide can be processed into N-bromosuccinimide (NBS) for reuse. In such simple post treatment operation, it is preferable to conduct the distillation under reduced pressure after removing the oxidizing substance such as the nitrogen-bromine bond-containing brominating agent or bromine ($Br_2$) remaining in the reaction terminated liquid or the filtrate by pretreatment with a reducing agent e.g. sodium thiosulfate or sodium hydrogen sulfite or an unsaturated compound e.g. 1-dodecene, α-methylstyrene or diallyl phthalate. (As the unsaturated compound, there may be suitably used those having a higher boiling point than that of the target 2-bromo-2-fluoropropionic ester.) This makes it possible to avoid a problem associated with the generation of bromine ($Br_2$) during the distillation. Further, the oxidizing substance, fluorine ions and water contained in the reaction terminated liquid, the filtrate or the crude product may be treated as appropriate with the above inorganic base (deacidification agent e.g. propylene oxide or cyclohexene oxide is suitable in some case), defluorinating agent or dehydrating agent e.g. magnesium sulfate, phosphorus pentaoxide or molecular sieve (dehydrating filter etc. is suitable in some cases).

The crude product can be purified to a high purity as needed by purification operation such as activated carbon treatment, fractional distillation, recrystallization or column chromatography. The crude product can alternatively be subjected as it is to the subsequent dehydrobromination step.

The dehydrobromination step will be next explained in detail below.

Examples of the base are: organic bases such as trimethylamine, triethylamine, diisopropylethylamine, tri-n-propylamine, tri-n-butylamine, tri-n-pentylamine, tri-n-hexylamine, pyridine, 2,3-lutidine, 2,4-lutidine, 2,5-lutidine, 2,6-lutidine, 3,4-lutidine, 3,5-lutidine, 2,3,4-collidine, 2,4,5-collidine, 2,5,6-collidine, 2,4,6-collidine, 3,4,5-collidine, 3,5,6-collidine, 4-dimethylaminopyridine (DMAP), 1,5-diazabicyclo[4.3.0]non-5-ene (DBN), 1,8-diazabicyclo[5.4.0]undec-7-ene (DBU), N,N,N',N',N"-pentamethylguanidine, 1,5,7-triazabicyclo[4.4.0]deca-5-ene (TBD), BEMP and tert-Bu-P4; and inorganic bases such as lithium hydrogencarbonate, sodium hydrogencarbonate, potassium hydrogencarbonate, cesium hydrogencarbonate, lithium carbonate, sodium carbonate, potassium carbonate and cesium carbonate. These bases can be used solely or in combination thereof.

For the purpose of low-cost production, it is preferable to use an alkali metal carbonate or tri-n-butylamine stoichiometrically in the presence of a catalytic amount of 1,8-diazabicyclo[5.4.0]undec-7-ene (DBU) and is particularly preferable to an alkali metal carbonate (more preferably sodium carbonate or potassium carbonate, still more preferably potassium carbonate) stoichiometrically in the presence of a catalytic amount of 1,8-diazabicyclo[5.4.0]undec-7-ene (DBU). The combined use of such preferred bases makes it possible that: the amount of use of the expensive 1,8-diazabicyclo[5.4.0]undec-7-ene (DBU) can be significantly reduced; and the target 2-fluoroacrylic ester of the general formula [3] can be isolated by simple operation e.g. filtering the reaction terminated liquid as needed and distilling the filtrate directly. On the other hand, it is not preferable to use an alkali metal hydroxide such as lithium hydroxide, sodium hydroxide, potassium hydroxide or cesium hydroxide as there occurs hydrolysis of the ester moiety by the use of the alkali metal hydroxide.

It suffices to use the base in an amount of 0.6 mol or more per 1 mol of the 2-bromo-2-fluoropropionic ester of the general formula [2]. The amount of the base used is preferably 0.7 to 5 mol, more preferably 0.8 to 3 mol, per 1 mol of the 2-bromo-2-fluoropropionic ester of the general formula [2].

In the case of using the alkali metal carbonate or tri-n-butylamine stoichiometrically in the presence of a catalytic amount of 1,8-diazabicyclo[5.4.0]undec-7-ene (DBU), it suffices that the amount of 1,8-diazabicyclo[5.4.0]undec-7-ene (DBU) used is 0.5 mol or less per 1 mol of the 2-bromo-2-fluoropropionic ester of the general formula [2]. The amount of 1,8-diazabicyclo[5.4.0]undec-7-ene (DBU) used is preferably 0.01 to 0.4 mol, more preferably 0.03 to 0.3 mol, per 1 mol of the 2-bromo-2-fluoropropionic ester of the general formula [2]. There is a tendency that the amount of 2,2-difluoropropionic ester (estimated structure) by-produced as an impurity increases with decrease in the amount of 1,8-diazabicyclo[5.4.0]undec-7-ene (DBU) used. This impurity is extremely difficult to separate by fractional distillation from the target 2-fluoroacrylic ester of the general formula [3]. It is thus particularly preferable to use 0.1 mol or more of 1,8-diazabicyclo[5.4.0]undec-7-ene (DBU) per 1 mol of the 2-bromo-2-fluoropropionic ester of the general formula [2]. The amount of the alkali metal carbonate or tri-n-butylamine used is adjusted in such a manner that the sum of the amount of the alkali metal carbonate or tri-n-butylamine and the catalytic amount of 1,8-diazabicyclo[5.4.0]undec-7-ene (DBU) falls within the above base amount.

Further, a polymerization inhibitor may be used. Examples of the polymerization inhibitor are phenothiazine, hydroquinone, 2,6-di-tert-butyl-4-methylphenol (BHT), methoquinone, tert-butylhydroquinone (TBH), 2,5-di-tert-butylhydroquinone, 1,2,4-trihydroxybenzene, leucoquinizarine, Nonflex F, Nonflex H, Nonflex DCD, Nonflex MBP, [2,2'-methylene-bis(4-methyl-6-tert-butylphenol)], Ozonone 35, tetraethylthiuramdisulfide, Q-1300, Q-1301, chloranil and sulfur. These polymerization inhibitors are commercially available and can be easily obtained on a large scale and at low cost. Among others, phenothiazine, hydroquinone and 2,6-di-tert-butyl-4-methylphenol (BHT) are preferred. Particularly preferred are phenothiazine and 2,6-di-tert-butyl-4-methylphenol (BHT).

It suffices to use the polymerization inhibitor in an amount of 0.00001 mol or more per 1 mol of the 2-bromo-2-fluoropropionic ester of the general formula [2]. The amount of the polymerization inhibitor used is preferably 0.0001 to 0.1 mol, more preferably 0.001 to 0.05 mol, per 1 mol of the 2-bromo-2-fluoropropionic ester of the general formula [2]. In the present reaction step, the use of the polymerization inhibitor is not essential but is effective for large-scale production.

There can also be used a reaction solvent. Examples of the reaction solvent are: aliphatic hydrocarbon solvents such as n-hexane and n-heptane; aromatic hydrocarbon solvents such as toluene and xylene; halogenated solvents such as methylene chloride and 1,2-dichloroethane; ether solvents such as tetrahydrofuran and tert-butyl methyl ether; ester solvents such as ethyl acetate and n-butyl acetate; amide solvents such as formamide, N,N-dimethylformamide, N,N-dimethylacetamide, 1-methyl-2-pyrrolidinone and 1,3-dimethyl-2-imidazolidinone; nitrile solvents such as acetonitrile and propionitrile; and sulfur oxide solvents such as dimethyl sulfoxide and sulfolane. Among others, n-heptane, toluene, methylene chloride, tetrahydrofuran, ethyl acetate, formamide, N,N-dimethylformamide, N,N-dimethylacetamide, 1-methyl-2-pyrrolidinone, 1,3-dimethyl-2-imidazolidinone, acetonitrile and dimethyl sulfoxide are preferred. Particularly preferred are formamide, N,N-dimethylformamide, N,N-dimethylacetamide, 1-methyl-2-pyrrolidinone, 1,3-dimethyl-2-imidazolidinone and dimethyl sulfoxide. These reaction solvents can be used solely or in combination thereof.

It suffices to use the reaction solvent in an amount of 0.05 L or more per 1 mol of the 2-bromo-2-fluoropropionic ester of the general formula [2]. The amount of the reaction solvent used is preferably 0.1 to 5 L, more preferably 0.15 to 4 L, per 1 mol of the 2-bromo-2-fluoropropionic ester of the general formula [2]. There is a tendency that the amount of 2,2-difluoropropionic ester (estimated structure) by-produced as the impurity increases as the amount of the reaction solvent used becomes very small. It is thus particularly preferable to use 0.3 L or more of the reaction solvent per 1 mol of the 2-bromo-2-fluoropropionic ester of the general formula [2].

It suffices that the reaction temperature is in the range of −30 to +120° C. The reaction temperature is preferably in the range of −20 to +110° C., more preferably −10 to +100° C.

It suffices that the reaction time is in the range of 24 hours or less. As the reaction time varies depending on the raw substrate material, the reagent, the reaction aid and the reaction conditions, it is desirable to determine the time at which there can be seen almost no consumption of the raw substrate material as the end of the reaction while monitoring the progress of the reaction by any analytical means such as gas chromatography, liquid chromatography or nuclear magnetic resonance.

The target 2-fluoroacrylic ester of the general formula [3] can be obtained from the reaction terminated liquid by any ordinary post treatment operation for organic synthesis.

Preferably, it is feasible to recover a crude product of the 2-fluoroacrylic ester by filtering out any solid matter from the reaction terminated liquid (after depositing the solid matter by cooling as needed), and then, directly subjecting the resulting filtrate to distillation under reduced pressure. Most of the recovered solid matter is hydrobromate of organic base or bromide of alkali metal. The former can be processed (regenerated) for reuse by neutralization and optionally purification, dehydration etc. In this regeneration operation, suitably used is tri-n-butylamine that shows high lipid solubility and has an adequate boiling point for distillation purification.

Fluorine ions or water contained in the reaction terminated liquid, the filtrate or the crude product can be treated as appropriate by the use of the same defluorinating agent or dehydrating agent as that of the bromination step. Further, the crude product can be purified to a high purity by purification operation such as activated carbon treatment, fractional distillation, recrystallization or column chromatography. In the case of using the alkali metal carbonate stoichiometrically in the presence of the catalytic amount of 1,8-diazabicyclo[5.4.0]undec-7-ene (DBU), there is a tendency that the 2-fluoroacrylic ester of the general formula [3] has a high water content as the boiling point of the 2-fluoroacrylic ester, in particular, the boiling point of the methyl ester is close to the boiling point of water. The water content of the 2-fluoroacrylic ester can be reduced effectively by the use of the dehydrating agent. In the case of using the alkali metal carbonate as the base, there occurs as a by-product of neutralization of hydrogen bromide generated during the progress of the reaction. It is an important finding of the present invention that the ester moiety of the target compound undergoes almost no hydrolysis even though the water is present in the reaction system under the basic conditions.

It is preferably feasible to adopt aeration distillation. The adoption of the aeration distillation makes it possible to effectively prevent self-polymerization of the 2-fluoroacrylic ester of the general formula [3] in a gas phase. As the polymerization inhibitor is effective in preventing the self-polymerization of the 2-fluoroacrylic ester of the general formula [3] in a liquid phase, the adoption of the aeration distillation in combination with the polymerization inhibitor is expected to produce the synergistic effects of preventing the self-polymerization of the 2-fluoroacrylic ester during the distillation purification. The aeration distillation can be suitably applied to the preferred embodiment that the post treatment operation of the dehydrobromination step is carried out by filtering out the solid matter from the reaction terminated liquid and directly subjecting the filtrate to distillation under reduced pressure. The term "distillation purification" used in the claims thus includes recovering the target product by directly subjecting the filtrate to reduced-pressure distillation. The amount of the oxygen introduced in the aeration distillation is not particular limited and can be adjusted in such a manner as not to cause an explosion in the whole of the distillation system including not only distillation equipment but also depressurization and exhaust mechanisms. The amount of the oxygen introduced is preferably 90% or less of the limiting oxygen concentration, more preferably 80% or less of the limiting oxygen concentration. On the other hand, the desired effects cannot be obtained when the amount of the oxygen introduced is extremely low. The amount of the oxygen introduced is thus preferably 0.0001% or more of the limiting oxygen concentration, more preferably 0.001% or more of the limiting oxygen concentration. In the case of introducing the air, the amount of the air introduced can be determined on the assumption that the concentration of oxygen in the air is 21%. The limiting oxygen concentration varies depending on R (alkyl group or fluorine-substituted alkyl group) of the 2-fluoroacrylic ester of the general formula [3], but can be estimated as about 10% as a guide.

EXAMPLES

The present invention will be described in more detail below by way of the following examples. It should be herein noted that these examples are illustrative and are not intended to limit the present invention thereto. In the following chemical formulas, Me represents a methyl group; and Et represents an ethyl group.

Example 1

To 24 mL of carbon tetrachloride, 2.50 g (23.6 mmol, 1.00 eq) of methyl 2-fluoropropionate of the following formula, 4.19 g (23.5 mmol, 1.00 eq) of N-bromosuccinimide (NBS) and 77.0 mg (0.469 mmol, 0.02 eq) of 2,2'-azobisisobutyronitrile (AIBN) were added.

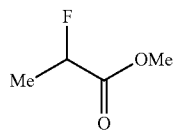

[Chem. 7]

The resulting reaction liquid was stirred for 2 days under reflux conditions. After 6 hours of stirring, 140 mg (0.853 mmol, 0.04 eq) of 2,2'-azobisisobutyronitrile (AIBN) was added to the reaction liquid. Further, 100 mg (0.609 mmol, 0.03 eq) of 2,2'-azobisisobutyronitrile (AIBN) was added to the reaction liquid after one night of stirring. (The total amount of 2,2'-azobisisobutyronitrile (AIBN) used was 0.09 eq.) The conversion rate of the reaction terminated liquid was determined by $^{19}$F-NMR to be 81%. The reaction terminated liquid was cooled in an ice cooling bath, followed by filtering out succinimide and washing the filtration residue with 5 mL of ethyl acetate. The thus-obtained filtrate was subjected concentration under reduced pressure (bath temperature: 30° C., reduced pressure level: 6 kPa). By this, 3.61 g of a crude product of methyl 2-bromo-2-fluoropropionate of the following formula was obtained.

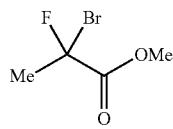

[Chem. 8]

The gas chromatographic purity of the crude product was 70.9%; and the yield of the crude product on a purity basis was 59%.

Example 2

To 416 mL of carbon tetrachloride, 100 g (833 mmol, 1.00 eq) of ethyl 2-fluoropropionate of the following formula, 163 g (916 mmol, 1.10 eq) of N-bromosuccinimide (NBS), 13.5 g (water content: 25%, 41.8 mmol, 0.05 eq) of benzoyl peroxide (BPO) and 13.3 g (83.2 mmol, 0.10 eq) of bromine (Br$_2$) were added.

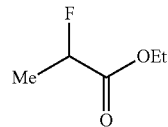

[Chem. 9]

The resulting reaction liquid was stirred for 1 hour under reflux conditions. The rate of conversion to ethyl 2-bromo-2-fluoropropionate of the following formula in the reaction terminated liquid was determined by gas chromatography to be 74%.

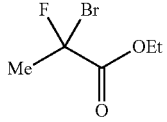

[Chem. 10]

Example 3

To 50 mL of 2,4-dichlorobenzotrifluoride, 10.0 g (94.3 mmol, 1.00 eq) of methyl 2-fluoropropionate of the following formula, 16.8 g (94.4 mmol, 1.00 eq) of N-bromosuccinimide (NBS) and 619 mg (3.77 mmol, 0.04 eq) of 2,2'-azobisisobutyronitrile (AIBN) were added.

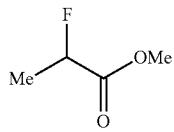

[Chem. 11]

The resulting reaction liquid was stirred for 4 days at 80° C. On the second day of stirring, 1.24 g (7.55 mmol, 0.08 eq) of 2,2'-azobisisobutyronitrile (AIBN) was added to the reaction liquid. Further, 5.04 g (28.3 mmol, 0.30 eq) of N-bromosuccinimide (NBS) and 619 mg (3.77 mmol, 0.04 eq) of 2,2'-azobisisobutyronitrile (AIBN) were added to the reaction liquid on the third day of stirring. (The total amount of N-bromosuccinimide (NBS) used was 1.30 eq; and the total amount of 2,2'-azobisisobutyronitrile (AIBN) used was 0.16 eq.) The conversion rate of the reaction terminated liquid was determined by $^{19}$F-NMR to be 92%. The reaction terminated liquid was cooled in an ice cooling bath, followed by filtering out succinimide and washing the filtration residue with a small amount of 2,4-dichlorobenzotrifluoride. The thus-obtained filtrate was directly subjected to simple distillation (flash distillation). By this, 37.7 g of a 2,4-dichlorobenzotrifluoride solution containing methyl 2-bromo-2-fluoropropionate of the following formula was obtained.

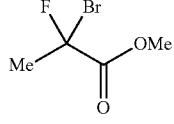

[Chem. 12]

The amount of the methyl 2-bromo-2-fluoropropionate contained in the 2,4-dichlorobenzotrifluoride solution was determined by $^{19}$F-NMR (quantification according to internal standard method) to be 11.6 g (62.7 mmol); and the yield of the methyl 2-bromo-2-fluoropropionate was 66%.

Example 4

To 800 mL of α,α,α,-trifluorotoluene (BTF), 400 g (3.77 mol, 1.00 eq) of methyl 2-fluoropropionate of the following formula, 805 g (4.52 mol, 1.20 eq) of N-bromosuccinimide (NBS) and 36.9 g (151 mmol, 0.04 eq) of 1,1'-azobis(cyclohexane-1-carbonitrile) (V-40) were added.

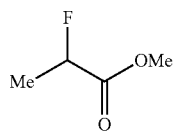

[Chem. 13]

The resulting reaction liquid was stirred for 2 days at 85 to 90° C. The conversion rate of the reaction terminated liquid was determined by $^{19}$F-NMR to be 85%. The reaction terminated liquid was cooled in an ice cooling bath. Any oxidizing substance in the reaction terminated liquid was treated by the addition of 46.4 g (188 mmol, 0.05 eq) of diallyl phthalate, followed by filtering out succinimide from the treated liquid and washing the filtration residue with 50 mL of α,α,α,-trifluorotoluene (BTF). The thus-obtained filtrate was directly subjected to simple distillation (flash distillation, boiling point: 55 to 64° C., reduced pressure level: 10 to 2 kPa). By this, 1.60 kg of an α,α,α,-trifluorotoluene (BTF) solution containing methyl 2-bromo-2-fluoropropionate of the following formula was obtained.

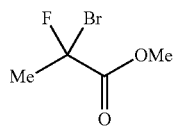

[Chem. 14]

The amount of the methyl 2-bromo-2-fluoropropionate contained in the α,α,α,-trifluorotoluene (BTF) solution was determined by $^{19}$F-NMR (quantification according to internal standard method) to be 573 g (3.10 mol); and the yield of the methyl 2-bromo-2-fluoropropionate was 82%.

Example 5

To 1.2 L of α,α,α,-trifluorotoluene (BTF), 600 g (5.66 mol, 1.00 eq) of methyl 2-fluoropropionate of the following formula, 1.20 kg (6.74 mol, 1.19 eq) of N-bromosuccinimide (NBS) and 27.6 g (113 mmol, 0.02 eq) of 1,1'-azobis(cyclohexane-1-carbonitrile) (V-40) were added.

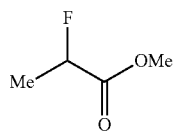

[Chem. 15]

The resulting reaction liquid was stirred for 22 hours and 30 minutes at 85 to 90° C. After 4 hours of stirring and after 8 hours of stirring, 6.90 g (28.2 mmol, 0.005 eq) of 1,1'-azobis (cyclohexane-1-carbonitrile) (V-40) was added to the reaction liquid. (The total amount of 1,1'-azobis(cyclohexane-1-carbonitrile) (V-40) used was 0.03 eq.) The conversion rate of the reaction terminated liquid was determined by $^{19}$F-NMR to be 79%. The reaction terminated liquid was cooled in an ice cooling bath. The reaction terminated liquid was stirred with 70.0 g (284 mmol, 0.05 eq) of diallyl phthalate for 1 hour at the same temperature to treat any oxidizing substance in the reaction terminated liquid, followed by filtering out succinimide from the treated liquid and washing the filtration residue with a small amount of α,α,α,-trifluorotoluene (BTF). The thus-obtained filtrate was directly subjected to simple distillation (flash distillation, boiling point: up to 50° C., reduced pressure level: up to 5 mmHg). By this, 2.90 kg of an α,α,α,-trifluorotoluene (BTF) solution containing methyl 2-bromo-2-fluoropropionate of the following formula was obtained.

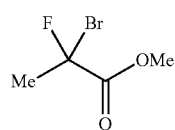

[Chem. 16]

The amount of the methyl 2-bromo-2-fluoropropionate contained in the α,α,α,-trifluorotoluene (BTF) solution was determined by $^{19}$F-NMR (quantification according to internal standard method) to be 775 g (4.19 mol); and the yield of the methyl 2-bromo-2-fluoropropionate was 74%.

Example 6

To 400 g (3.77 mol, 2.01 eq) of methyl 2-fluoropropionate of the following formula, 335 g (1.88 mol, 1.00 eq) of N-bromosuccinimide (NBS) and 15.7 g (water content: 25%, 48.6 mmol, 0.03 eq) of benzoyl peroxide (BPO) were added.

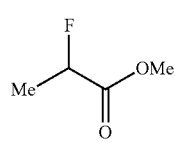

[Chem. 17]

The resulting reaction liquid was stirred for 2 days at 80° C. (The stirring was conducted very favorably.) After one night of stirring, 12.7 g (water content: 25%, 39.3 mmol, 0.02 eq) of benzoyl peroxide (BPO) was added to the reaction liquid. (The total amount of benzoyl peroxide used was 0.05 eq.) The reaction terminated liquid was cooled in an ice cooling bath, followed by filtering out succinimide and washing the filtration residue with 100 g of methyl 2-fluoropropionate. The thus-obtained filtrate was directly subjected to simple distillation (flash distillation, boiling point: 55 to 64° C., reduced pressure level: 10 kPa). By this, 600 g of a methyl 2-fluoropropionate solution containing methyl 2-bromo-2-fluoropropionate of the following formula was obtained.

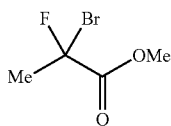
[Chem. 18]

The amount of the methyl 2-bromo-2-fluoropropionate contained in the methyl 2-fluoropropionate solution was determined by $^{19}$F-NMR (quantification according to internal standard method) to be 220 g (1.19 mol); and the yield of the methyl 2-bromo-2-fluoropropionate was 63%.

Example 7

To 400 g (3.77 mol, 3.99 eq) of methyl 2-fluoropropionate of the following formula, 168 g (944 mmol, 1.00 eq) of N-bromosuccinimide (NBS) and 9.18 g (37.6 mmol, 0.04 eq) of 1,1'-azobis(cyclohexane-1-carbonitrile) (V-40) were added.

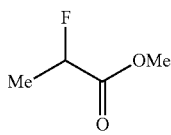
[Chem. 19]

The resulting reaction liquid was stirred for one night at 80° C. (The stirring was conducted very favorably.) The reaction terminated liquid was cooled in an ice cooling bath. Any oxidizing substance in the reaction terminated liquid was treated by the addition of 20.0 g (169 mmol, 0.18 eq) of α-methylstyrene, followed by filtering out succinimide from the treated liquid and washing the filtration residue with 50 g of methyl 2-fluoropropionate. The thus-obtained filtrate was directly subjected to simple distillation (flash distillation). By this, 467 g of a methyl 2-fluoropropionate solution containing methyl 2-bromo-2-fluoropropionate of the following formula was obtained.

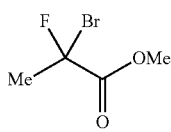
[Chem. 20]

The amount of the methyl 2-bromo-2-fluoropropionate contained in the methyl 2-fluoropropionate solution was determined by $^{19}$F-NMR (quantification according to internal standard method) to be 137 g (742 mmol); and the yield of the methyl 2-bromo-2-fluoropropionate was 79%.

Example 8

Produced was 2.8 kg of a methyl 2-fluoropropionate solution containing methyl 2-bromo-2-fluoropropionate of the following formula in a similar manner with reference to Examples 1 to 7 (content amount of methyl 2-bromo-2-fluoropropionate: 1.05 kg (5.68 mol) as determined by $^{19}$F-NMR (quantification according to internal standard method), gas chromatographic purity: 24.9%).

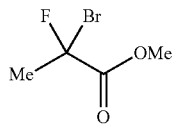
[Chem. 21]

This methyl 2-fluoropropionate solution was subjected to fractional distillation (theoretical plate number: 30, boiling point: 69 to 71° C., reduced pressure level: 9.1 kPa, reflux ratio: 80:1 to 2:1), thereby yielding 805 g of a main fraction of methyl 2-bromo-2-fluoropropionate. The recovery rate of the main fraction on a purity basis was 76%. The gas chromatographic purity of the main fraction was 98.8%. In the main fraction, there was contained 1.2% of α-methylstyrene used for treatment of the oxidizing substance. Even when the methyl 2-bromo-2-fluoropropionate containing such a small amount of α-methylstyrene was subjected to the subsequent dehydrobromination step, the α-methylstyrene could be easily removed by fractional distillation of the resulting methyl 2-fluoroacrylate. Further, the excessively used methyl 2-fluoropropionate was recovered with high purity and yield as an initial fraction by the fractional distillation and could be reused after dehydrated by a molecular sieve etc. as needed. Herein, the methyl 2-fluoropropionate solution of the methyl 2-bromo-2-fluoropropionate subjected to the fractional distillation was that (pH: neutral) obtained by simple distillation and acidic substance pretreatment with magnesium oxide.

The $^1$H-NMR and $^{19}$F-NMR data of the methyl 2-bromo-2-fluoropropionate are indicated below.

$^1$H-NMR [reference material: $(CH_3)_4Si$, deuterated solvent: $CDCl_3$] δ ppm; 2.27 (d, 19.6 Hz, 3H), 3.90 (s, 3H).

$^{19}$F-NMR [reference material: $C_6F_6$, deuterated solvent: $CDCl_3$] δ ppm; 53.34 (q, 19.3 Hz, 1F).

In each of Examples 9 to 14, 2-bromo-2-fluoropropionate was provided in a similar manner with reference to Examples 1 to 8.

Example 9

To 5 mL of N,N-dimethylformamide, 1.00 g (gas chromatographic purity: 84.1%, 4.55 mmol, 1.00 eq) of methyl 2-bromo-2-fluoropropionate of the following formula, 988 mg (6.49 mmol, 1.43 eq) of 1,8-diazabicyclo[5.4.0]undec-7-ene (DBU) and 10.0 mg (0.0502 mmol, 0.01 eq) of phenothiazine were added.

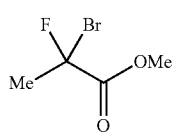
[Chem. 22]

The resulting reaction liquid was stirred for 2 hours at 60° C. The conversion rate of the reaction terminated liquid was determined by $^{19}$F-NMR to be 100%. The amount of methyl 2-fluoroacrylate of the following formula contained in the reaction terminated liquid was determined by $^{19}$F-NMR (quantification according to internal standard method) to be 409 mg (3.93 mmol); and the yield of the methyl 2-fluoroacrylate was 86%.

[Chem. 23]

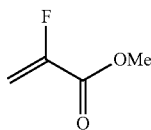

The amount of methyl 2,2-difluoropropionate (estimated structure) generated as a by-product was determined by $^{19}$F-NMR to be methyl 2-fluoroacrylate:methyl 2,2-difluoropropionate=1:0.01.

Example 10

To a tetrahydrofuran solution (solvent amount: 188 mL) containing 46.1 g (gas chromatographic purity: 88.2%, 204 mmol, 1.00 eq) of ethyl 2-bromo-2-fluoropropionate of the following formula, a tetrahydrofuran solution (solvent amount: 43 mL) containing 42.9 g (282 mmol, 1.38 eq) of 1,8-diazabicyclo[5.4.0]undec-7-ene (DBU) was gradually added.

[Chem. 24]

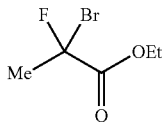

The resulting reaction liquid was stirred for one night at 35° C. The rate of conversion to ethyl 2-fluoroacrylate of the following formula in the reaction terminated liquid was determined by gas chromatography to be 100%.

[Chem. 25]

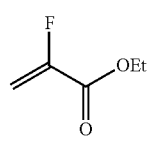

Example 11

To 160 mL of N,N-dimethylformamide, 30.0 g (gas chromatographic purity: 83.7%, 136 mmol, 1.00 eq) of methyl 2-bromo-2-fluoropropionate of the following formula, 1.22 g (8.01 mmol, 0.06 eq) of 1,8-diazabicyclo[5.4.0]undec-7-ene (DBU), 22.4 g (162 mmol, 1.19 eq) of potassium carbonate and 300 mg (1.36 mmol, 0.01 eq) of 2,6-di-tert-butyl-4-methylphenol (BHT) were added.

[Chem. 26]

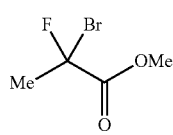

The resulting reaction liquid was stirred for 5 hours at 60° C. The conversion rate of the reaction terminated liquid was determined by $^{19}$F-NMR to be 87%. The reaction terminated liquid was cooled, followed by filtering out a solid matter and washing the filtration residue with a small amount of N,N-dimethylformamide. The thus-obtained filtrate was admixed with 1.50 g (6.81 mmol, 0.05 eq) of 2,6-di-tert-butyl-4-methylphenol (BHT) and then subjected to simple distillation (flash distillation, boiling point: 34 to 50° C., reduced pressure level: 2 kPa). By this, 123 g of a N,N-dimethylformamide solution containing methyl 2-fluoroacrylate of the following formula was obtained. Herein, 200 mg (0.908 mmol, 0.007 eq) of 2,6-di-tert-butyl-4-methylphenol (BHT) was added in advance to theisolating distillation fraction.

[Chem. 27]

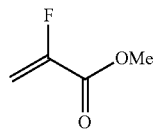

The amount of the methyl 2-fluoroacrylate contained in the N,N-dimethylformamide solution was determined by $^{19}$F-NMR (quantification according to internal standard method) to be 11.6 g (111 mmol); and the yield of the methyl 2-fluoroacrylate was 82%. The amount of methyl 2,2-difluoropropionate (estimated structure) generated as a by-product was determined by $^{19}$F-NMR to be methyl 2-fluoroacrylate:methyl 2,2-difluoropropionate=1:0.04.

Example 12

To 5 mL of N,N-dimethylformamide, 1.00 g (gas chromatographic purity: 84.1%, 4.55 mmol, 1.00 eq) of methyl 2-bromo-2-fluoropropionate of the following formula, 41.0 mg (0.269 mmol, 0.06 eq) of 1,8-diazabicyclo[5.4.0]undec-7-ene (DBU), 1.00 g (5.40 mmol, 1.19 eq) of tri-n-butylamine and 10.0 mg (0.0502 mmol, 0.01 eq) of phenothiazine were added.

[Chem. 28]

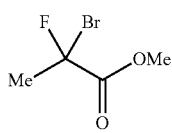

The resulting reaction liquid was stirred for 5 hours at 70° C. The conversion rate of the reaction terminated liquid was determined by $^{19}$F-NMR to be 61%. The amount of methyl 2-fluoroacrylate of the following formula contained in the reaction terminated liquid was determined by $^{19}$F-NMR (quantification according to internal standard method) to be 325 mg (3.12 mmol); and the yield of the methyl 2-fluoroacrylate was 69%.

[Chem. 29]

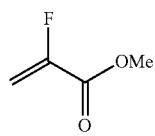

The amount of methyl 2,2-difluoropropionate (estimated structure) generated as a by-product was determined by $^{19}$F-NMR to be methyl 2-fluoroacrylate:methyl 2,2-difluoropropionate=1:0.13.

Example 13

To 5 mL of N,N-dimethylformamide, 1.00 g (gas chromatographic purity: 84.1%, 4.55 mmol, 1.00 eq) of methyl 2-bromo-2-fluoropropionate of the following formula, 82.0 mg (0.539 mmol, 0.12 eq) of 1,8-diazabicyclo[5.4.0]undec-7-ene (DBU), 750 mg (5.43 mmol, 1.19 eq) of potassium carbonate and 10.0 mg (0.0502 mmol, 0.01 eq) of phenothiazine were added.

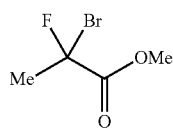

[Chem. 30]

The resulting reaction liquid was stirred for 5 hours at 70° C. The conversion rate of the reaction terminated liquid was determined by $^{19}$F-NMR to be 100%. The amount of methyl 2-fluoroacrylate of the following formula contained in the reaction terminated liquid was determined by $^{19}$F-NMR (quantification according to internal standard method) to be 444 mg (4.27 mmol); and the yield of the methyl 2-fluoroacrylate was 94%.

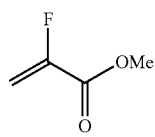

[Chem. 31]

The amount of methyl 2,2-difluoropropionate (estimated structure) generated as a by-product was determined by $^{19}$F-NMR to be methyl 2-fluoroacrylate:methyl 2,2-difluoropropionate=1:0.01.

Example 14

Produced was 854 g of a N,N-dimethylformamide solution containing methyl 2-fluoroacrylate of the following formula in a similar manner with reference to Examples 9 to 13 (content amount of methyl 2-fluoroacrylate: 89.8 g (863 mmol) as determined by $^{19}$F-NMR (quantification according to internal standard method), amount of methyl 2,2-difluoropropionate (estimated structure) generated as by-product: methyl 2-fluoroacrylate:methyl 2,2-difluoropropionate=1:0.08 as determined by $^{19}$F-NMR, gas chromatographic purity: 10.6%).

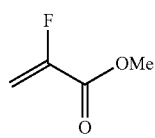

[Chem. 32]

This N,N-dimethylformamide solution was subjected to fractional distillation (theoretical plate number: 30, boiling point: 29 to 31° C., reduced pressure level: 9.1 kPa, reflux ratio: 60:1 to 20:1), thereby yielding 66.6 g of a main fraction of methyl 2-fluoroacrylate. The amount of the methyl 2-fluoroacrylate contained in the main fraction was determined by $^{19}$F-NMR (quantification according to internal standard method) to be 60.2 g (578 mmol). The recovery rate of the main fraction on a purity basis was 67%. The gas chromatographic purity of the main fraction was 97.3%. In the main fraction, there was contained 2.7% of methyl 2,2-difluoropropionate. As the water content of the main fraction was high (0.9%), the main fraction was dehydrated by a molecular sieve 4A (the molecular sieve was used in an amount of 560 mg per 1.00 g of the main fraction; and the main fraction was left together with the molecular sieve for 2 days). (The water content of the dehydrated main fraction was 0.0%.) Herein, the fractional distillation was conducted in the presence of 2,6-di-tert-butyl-4-methylphenol (BHT). More specifically, 1.90 g (8.63 mmol, 0.01 eq) of 2,6-di-tert-butyl-4-methylphenol (BHT) was added in advance to each of the bottom and top of the distillation column and the isolating distillation fraction. (The total amount of 2,6-di-tert-butyl-4-methylphenol (BHT) additionally used was 0.03 eq.)

The $^1$H-NMR and $^{19}$F-NMR data of the methyl 2-fluoroacrylate are indicated below.

$^1$H-NMR [reference material: (CH$_3$)$_4$Si, deuterated solvent: CDCl$_3$] δ ppm; 3.85 (s, 3H), 5.36 (dd, 13.2 Hz, 3.2 Hz, 1H), 5.69 (dd, 3.2 Hz, 44.0 Hz, 1H).

$^{19}$F-NMR [reference material: C$_6$F$_6$, deuterated solvent: CDCl$_3$] δ ppm; 44.67 (dd, 42.7 Hz, 13.7Hz, 1F).

The $^1$H-NMR and $^{19}$F-NMR data and mass chromatography (MS) data of the methyl 2,2-difluoropropionate (estimated structure) are also indicated below.

$^1$H-NMR [reference material: (CH$_3$)$_4$Si, deuterated solvent: CDCl$_3$] δ ppm; 1.81 (t, 18.8 Hz, 3H), 3.88 (s, 3H).

$^{19}$F-NMR [reference material: C$_6$F$_6$, deuterated solvent: CDCl$_3$] δ ppm; 62.90 (q, 18.3 Hz, 2F).

MS; EI/124 (M+), 81, 65, 59, CI/125 (M+H).

Example 15

To 170 L of α,α,α,-trifluorotoluene (BTF), 85.0 kg (801 mol, 1.00 eq) of methyl (R)-2-fluoropropionate, 171 kg (961 mol, 1.20 eq) of N-bromosuccinimide (NBS) and 1.17 kg (4.79 mol, 0.006 eq) of 1,1'-azobis(cyclohexane-1-carbonitrile) (V-40) were added.

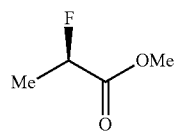

[Chem. 33]

The resulting reaction liquid was stirred for 35 hours at 85 to 90° C. After 5 hours of stirring, after 10 hours of stirring, after 15 hours of stirring and after 20 hours of stirring, 1.17 kg (4.79 mol, 0.006 eq) of 1,1'-azobis(cyclohexane-1-carbonitrile) (V-40) was added to the reaction liquid. (The total amount of 1,1'-azobis(cyclohexane-1-carbonitrile) (V-40) used was 0.03 eq.) The conversion rate of the reaction terminated liquid was determined by $^{19}$F-NMR to be 92%. The reaction terminated liquid was cooled down to room temperature. Any oxidizing substance in the reaction terminated liquid was treated by the addition of 20.0 kg (81.2 mol, 0.10 eq) of diallyl phthalate, followed by filtering out succinimide from the treated liquid and washing the filtration residue with 30 L of α,α,α,-trifluorotoluene (BTF). The thus-obtained filtrate was directly subjected to simple distillation (flash distillation). By this, 341 kg of an α,α,α,-trifluorotoluene (BTF) solution containing methyl 2-bromo-2-fluoropropionate of the following formula was obtained.

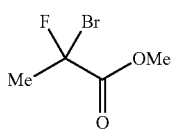

[Chem. 34]

The amount of the methyl 2-bromo-2-fluoropropionate contained in the α,α,α,-trifluorotoluene (BTF) solution was determined by $^{19}$F-NMR (quantification according to internal standard method) to be 115 kg (620 mol); and the yield of the methyl 2-bromo-2-fluoropropionate was 77%. The whole (341 kg) of the above-obtained α,α,α,-trifluorotoluene (BTF) solution containing the methyl 2-bromo-2-fluoropropionate was subjected to fractional distillation (theoretical plate number: 30, boiling point: 71° C., reduced pressure level: 9.1 kPa, reflux ratio: 2:1), thereby yielding 103 kg of a main fraction of methyl 2-bromo-2-fluoropropionate. The recovery rate of the main fraction was 90%. The gas chromatographic purity of the main fraction was 99.9%. The unreacted methyl (R)-2-fluoropropionate as the raw substrate material and the α,α,α,-trifluorotoluene (BTF) as the reaction solvent was recovered with high yield in the form of a mixture thereof as an initial fraction by the fractional distillation and could be reused after dried by a molecular sieve etc. as needed. The $^1$H-NMR and $^{19}$F-NMR data of the methyl 2-bromo-2-fluoropropionate were the same as those of Example 8.

Example 16

To 100 L of 1,3-dimethyl-2-imidazolidinone, 25.0 kg (135 mol, 1.00 eq) of methyl 2-bromo-2-fluoropropionate of the following formula produced in Example 15 and 250 g (1.25 mol, 0.009 eq) of phenothiazine were added. While controlling the inside temperature of the reaction system to be 35° C. or lower, 21.2 kg (139 mol, 1.03 eq) of 1,8-diazabicyclo[5.4.0]undec-7-ene (DBU) was added to the reaction liquid.

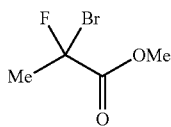

[Chem. 35]

The resulting reaction liquid was stirred for 2 hours at room temperature. For smooth deposition of hydrobromate of 1,8-diazabicyclo[5.4.0]undec-7-ene (DBU·Br), 160 g of DBU·HBr was added as a seed crystal at the time one quarter of the above predetermined amount of the DBU was dropped into the reaction liquid. The conversion rate of the reaction terminated liquid was determined by $^{19}$F-NMR to be 96%. The DBU·HBr was filtered out of the reaction terminated liquid. The thus-obtained filtrate was subjected to simple distillation (flash distillation (1 wt % 1,3-dimethyl-2-imidazolidinone solution of 2,6-di-tert-butyl-4-methylphenol (BHT) was added to the liquid accumulation portion of the distillation column), setting temperature: up to 89° C. (fraction 1), up to 123° C. (fraction 2), reduced pressure level: up to 3.0 kPa). By this, 19.6 kg in sum of two fractions of methyl 2-fluoroacrylate of the following formula was obtained. Herein, 30.0 g (136 mmol, 0.001 eq) of 2,6-di-tert-butyl-4-methylphenol (BHT) was added in advance to each of the receivers of the fractions. (The total amount of 2,6-di-tert-butyl-4-methylphenol (BHT) added was 0.002 eq.) Further, the fractions were recovered while stirring under ice cooling.

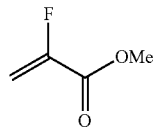

[Chem. 36]

The total amount of the methyl 2-fluoroacrylate contained was determined by $^{19}$F-NMR (quantification according to internal standard method) to be 11.4 kg (109 mol). (The remaining about 8 kg of the fractions was 1,3-dimethyl-2-imidazolidinone; and the amount of the 1,3-dimethyl-2-imidazolidinone contained in the fraction 2 was larger than that in the fraction 1.) The yield of the methyl 2-fluoroacrylate was 81%. The amount of methyl 2,2-difluoropropionate (estimated structure) generated as a by-product was determined by $^{19}$F-NMR to be methyl 2-fluoroacrylate:methyl 2,2-difluoropropionate=1:0.01.

The whole (8.44 kg) of the fraction 1 of the methyl 2-fluoroacrylate was dried by a molecular sieve 4A (5 wt %) for one night. (The amount of the methyl 2-fluoroacrylate contained in the fraction 1 was determined by $^{19}$F-NMR (quantification according to internal standard method) to be 7.17 kg (68.9 mol); the gas chromatographic purity of the methyl 2,2-difluoropropionate, methyl 2-fluoroacrylate and 1,3-dimethyl-2-imidazolidinone were 0.3%, 91.6% and 7.7%, respectively; and the water content of the fraction 1 was 0.15%.) The fraction 1 was then subjected to simple distillation using a rotary evaporator (flash distillation (500 ppm methyl 2-fluoroacrylate solution of 2,6-di-tert-butyl-4-methylphenol (BHT) was added to the liquid accumulation portion of the distillation column), setting temperature: up to 30° C., reduced pressure level: up to 20 kPa). There was thus obtained 7.52 kg of a purified product of the methyl 2-fluoroacrylate of the above formula. (The amount of product fraction exceeded the quantitative amount of charge due to accuracy errors in internal standard method;

2,6-di-tert-butyl-4-methylphenol (BHT) was added in advance to the receiver of the fraction in an amount of 200 ppm relative to the estimated fraction amount; and the fraction was recovered while stirring under ice cooling.) The gas chromatographic purity of the purified product was 99.3% (methyl 2,2-difluoropropionate (estimated structure): 0.3%, 1,3-dimethyl-2-imidazolidinone: 0.1%). The water content of the purified product was 0.08%. The concentration of the 2,6-di-tert-butyl-4-methylphenol (BHT) was 238 ppm (calculated value).

Further, the whole (11.2 kg) of the fraction 2 of the methyl 2-fluoroacrylate was treated twice by the same operation as that of the fraction 1. (The amount of the methyl 2-fluoroacrylate contained in the fraction 2 was determined by $^{19}$F-NMR (quantification according to internal standard method) to be 4.22 kg (40.5 mol); the gas chromatographic purity of the methyl 2,2-difluoropropionate, methyl 2-fluoroacrylate and 1,3-dimethyl-2-imidazolidinone were 0.2%, 38.3% and 61.0%, respectively; and the water content of the fraction 2 was 0.43%.) There was obtained 3.00 kg of a purified product of the methyl 2-fluoroacrylate of the above formula. The gas chromatographic purity of the purified product was 99.0% (methyl 2,2-difluoropropionate (estimated structure): 0.5%, 1,3-dimethyl-2-imidazolidinone: <0.1%). The water content of the purified product was 0.09%. The concentration of the 2,6-di-tert-butyl-4-methylphenol (BHT) was 250 ppm (calculated value). The total amount of the purified product obtained from the fractions 1 and 2 was 10.5 kg. The total yield of the purified product was 74%.

The $^1$H-NMR and $^{19}$F-NMR data of the methyl 2-fluoroacrylate were the same as those of Example 14.

Example 17

To distillation equipment, 128 g (1.23 mol, 1.00 eq) of methyl 2-fluoroacrylate of the following formula produced in a similar manner with reference to Examples 15 and 16 and 750 mg (3.40 mmol, 0.003 eq) of 2,6-di-tert-butyl-4-methylphenol (BHT) were added. (The gas chromatographic purity of the methyl 2-fluoroacrylate was 98.7%; and the concentration of 2,6-di-tert-butyl-4-methylphenol (BHT) in the methyl 2-fluoroacrylate was 227 ppm (calculated value).) The resulting liquid was placed under total reflux conditions (setting temperature: 72° C., bottom inside temperature: 53° C., reduced pressure level: 42.4 kPa, air introduction amount: 5 mL/min) for 8 hours and 55 minutes, and then, subjected to simple distillation (flash distillation (500 ppm methyl 2-fluoroacrylate solution of 2,6-di-tert-butyl-4-methylphenol (BHT) was not added to the liquid accumulation portion of the distillation column), setting temperature: 72° C., bottom inside temperature: 54° C., column top temperature: 50° C., reduced pressure level: 45.6 kPa, air introduction amount: 5 mL/min, time: 1 hour and 25 minutes). By this, 122 g of the methyl 2-fluoroacrylate was obtained. Herein, 2,6-di-tert-butyl-4-methylphenol (BHT) was added in advance to the receiver of the fraction in an amount of 200 ppm relative to the estimated fraction amount; and the fraction was recovered while stirring under ice cooling.)

[Chem. 37]

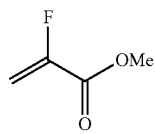

The recovery rate of the methyl 2-fluoroacrylate was 95%. The gas chromatographic purity of the methyl 2-fluoroacrylate was 98.9%. The $^1$H-NMR and $^{19}$F-NMR data of the methyl 2-fluoroacrylate were the same as those of Example 14 and showed that there was contained no product of self-polymerization of the methyl 2-fluoroacrylate. It was confirmed that, even though no polymerization inhibitor was added, it was possible to prevent self-polymerization of the methyl 2-fluoroacrylate throughout the distillation equipment (notably, in the liquid accumulation portion of the distillation column) by the adoption of the aeration distillation.

Example 18

A crude product of methyl 2-fluoroacrylate of the following formula was produced in a similar manner with reference to Examples 15 and 16. (The purity of the crude product was at a level corresponding to that obtained by, after filtering out hydrobromate of 1,8-diazabicyclo[5.4.0]undec-7-ene (DBU·HBr) from the reaction terminated liquid after the dehydrobromination step, simple distillation of the filtrate.) The crude product was subjected to aeration distillation in a similar manner with reference to Example 17, thereby yielding a purified product of the methyl-2-fluoroacrylate. The gas chromatographic purity of the purified product was 99.0% or higher. There was not seen self-polymerization of the methyl 2-fluoroacrylate at all.

[Chem. 38]

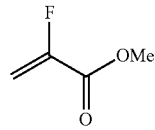

Although the present invention has been described with reference to the above specific embodiments, the present invention is not limited to these exemplary embodiments. Various modifications and variations of the embodiments described above can be made without departing from the scope of the present invention.

The invention claimed is:

1. A process of producing a 2-fluoroacrylic ester of the general formula [3], comprising:
   a bromination step of converting a 2-fluoropropionic ester of the general formula [1] to a 2-bromo-2-fluoropropionic ester of the general formula [2] by reaction of the 2-fluoropropionic ester with a nitrogen-bromine bond-containing brominating agent in the presence of a radical initiator; and
   a dehydrobromination step of reacting the 2-bromo-2-fluoropropionic ester with a base

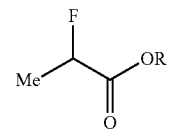

[1]

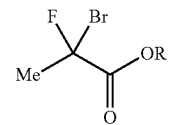

[2]

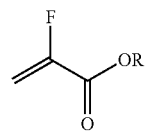

[3]

where Me represents a methyl group; and R represents an alkyl group or a fluorine-substituted alkyl group.

2. The process of producing the 2-fluoroacrylic ester according to claim 1, wherein, in an ester moiety of the ester, R is either a methyl group, an ethyl group, a 2,2,2-trifluoroethyl group or a 1,1,1,3,3,3-hexafluoroisopropyl group.

3. The process of producing the 2-fluoroacrylic ester according to claim 1, wherein the nitrogen-bromine bond-containing brominating agent used in the bromination step is N-bromosuccinimide (NBS).

4. The process of producing the 2-fluoroacrylic ester according to claim 1, wherein the radical initiator used in the bromination step is either 2,2'-azobisisobutyronitrile (AIBN), 1,1'-azobis(cyclohexane-1-carbonitrile) (V-40) or benzoyl peroxide (BPO).

5. The process of producing the 2-fluoroacrylic ester according to claim 1, wherein an alkali metal carbonate is used stoichiometrically in the presence of a catalytic amount of 1,8-diazabicyclo[5.4.0]undec-7-ene (DBU) as the base in the dehydrobromination step.

6. The process of producing the 2-fluoroacrylic ester according to claim 1, wherein tri-n-butylamine is used stoichiometrically in the presence of a catalytic amount of 1,8-diazabicyclo[5.4.0]undec-7-ene (DBU) as the base in the dehydrobromination step.

7. The process of producing the 2-fluoroacrylic ester according to claim 1, wherein the dehydrobromination step is performed in the presence of a polymerization inhibitor.

8. The process of producing the 2-fluoroacrylic ester according to claim 7, wherein the polymerization inhibitor is either phenothiazine, hydroquinone or 2,6-di-tert-butyl-4-methylphenol (BHT).

9. The process of producing the 2-fluoroacrylic ester according to claim 1, further comprising subjecting the 2-fluoroacrylic ester to distillation purification in the presence of a polymerization inhibitor.

10. The process of producing the 2-fluoroacrylic ester according to claim 9, wherein the polymerization inhibitor is either phenothiazine, hydroquinone or 2,6-di- tert-butyl-4-methylphenol (BHT).

11. The process of producing the 2-fluoroacrylic ester according to claim 1, further comprising subjecting the 2-fluoroacrylic ester to distillation purification while entraining air or oxygen in the 2-fluoroacrylic ester.

* * * * *